(12) United States Patent  
Konstandopoulos et al.

(10) Patent No.: US 8,234,858 B2
(45) Date of Patent: Aug. 7, 2012

(54) PARTICULATE MATTER CONCENTRATION MEASURING APPARATUS

(75) Inventors: Athanasios G. Konstandopoulos, Thessaloniki (GR); Fumishige Miyata, Gifu (JP); Takafumi Kasuga, Gifu (JP); Kazuhiro Ito, Gifu (JP)

(73) Assignees: Ibiden Co., Ltd., Ogaki-Shi (JP); Athanasios G. Konstandopoulos, Thessaloniki (GR)

( * ) Notice: Subject to any disclaimer, the term of this patent is extended or adjusted under 35 U.S.C. 154(b) by 398 days.

(21) Appl. No.: 12/694,288

(22) Filed: Jan. 27, 2010

(65) Prior Publication Data

US 2010/0242455 A1 Sep. 30, 2010

(30) Foreign Application Priority Data

Mar. 31, 2009 (WO) .................. PCT/JP2009/056749

(51) Int. Cl.
*F01N 3/00* (2006.01)
(52) U.S. Cl. .......................................... 60/311; 60/315
(58) Field of Classification Search .................... 60/288, 60/311, 315
See application file for complete search history.

(56) References Cited

U.S. PATENT DOCUMENTS

| | | | | |
|---|---|---|---|---|
| 5,656,048 | A * | 8/1997 | Smith et al. ................... 55/282 |
| 2008/0087011 | A1* | 4/2008 | Konstandopoulos ............ 60/311 |
| 2008/0087012 | A1* | 4/2008 | Konstandopoulos ............ 60/311 |
| 2008/0087101 | A1* | 4/2008 | Konstandopoulos ...... 73/861.42 |
| 2008/0098724 | A1* | 5/2008 | Konstandopoulos ............ 60/278 |
| 2009/0074630 | A1* | 3/2009 | Gonze et al. .................. 422/174 |
| 2011/0179778 | A1* | 7/2011 | Durrett .......................... 60/299 |

FOREIGN PATENT DOCUMENTS

| | | |
|---|---|---|
| EP | 1916394 | 4/2008 |
| JP | 3-258910 | 11/1991 |
| JP | 7-19027 | 1/1995 |
| JP | 8-28248 | 1/1996 |
| JP | 2002-285822 | 10/2002 |
| JP | 2008-101602 | 5/2008 |

* cited by examiner

*Primary Examiner* — Thomas Denion
*Assistant Examiner* — Patrick Maines
(74) *Attorney, Agent, or Firm* — Ditthavong Mori & Steiner, P.C.

(57) ABSTRACT

A particulate matter concentration measuring apparatus configured to measure a particulate matter concentration in exhaust gas includes an exhaust gas extraction line that is branched from an exhaust line and has a flow passage cross-sectional area smaller than that of the exhaust line, a particulate matter detection filter provided in the exhaust gas extraction line and configured to catch particulate matter, a heating unit configured to heat the caught particulate matter, and a differential pressure detection unit configured to detect a differential pressure generated between an inlet and an outlet of the particulate matter detection filter. The heating unit is configured to apply about 50% or more of a calorific value for heating the particulate matter to an area making up about 30% of the particulate matter detection filter on an upstream side of an exhaust gas flow.

14 Claims, 13 Drawing Sheets

PARTICULATE MATTER CONCENTRATION MEASURING APPARATUS

CROSS-REFERENCE TO RELATED APPLICATION

The present application claims priority under 35 U.S.C §119 to International Application No. PCT/JP2009/056749, filed on Mar. 31, 2009. The contents of this application are incorporated herein by reference in their entirety.

BACKGROUND OF THE INVENTION

1. Field of the Invention

The present invention relates to a particulate matter concentration measuring apparatus.

2. Discussion of Background

As a known apparatus that detects the concentration of particulate matter mainly containing C (carbon) in exhaust gas from a diesel engine, Patent Document 1 discloses a particulate matter concentration measuring apparatus 20PM (PM sensor) shown in FIG. 1. The particulate matter concentration measuring apparatus 20PM has a sub-exhaust line 21A branched from an exhaust line 21; a particulate matter detection filter 22A arranged in the sub-exhaust line 21A; and a differential pressure measuring unit 22B that measures a differential pressure generated between the inlet and the outlet of the particulate matter detection filter 22A. The sub-exhaust line 21A is provided with a flow measuring unit 24 and a temperature measuring unit T1, and the particulate matter detection filter 22A is provided with a heater.

The particulate matter concentration measuring apparatus 20PM of EP1916394A1 measures a differential pressure ΔP generated between the front side and the rear side of the particulate matter detection filter 22A, a temperature T of exhaust gas in the sub-exhaust line 21A, and a flow Q2 of the exhaust gas in the sub-exhaust line 21A. Based on the differential pressure ΔP, the temperature T, and the flow Q2 thus measured, the mass PM (g/h) of particulate matter caught by the particulate matter detection filter 22A per unit time is calculated. Furthermore, based on the mass PM (g/h) of the particulate matter, the concentration $PM_{conc}$ (g/m$^3$) of the particulate matter in the exhaust gas is calculated.

In addition, EP1916394A1 discloses a particulate matter catching filter (DPF: diesel particulate filter) 22 made of porous ceramics in the exhaust line 21 as a component of an exhaust gas purification apparatus 20. The sub-exhaust line 21A of the particulate matter concentration measuring apparatus 20PM is connected to the upstream side of the exhaust gas flow of the particulate matter catching filter (DPF) 22. Based on the concentration $PM_{conc}$ (g/m$^3$) of the particulate matter in the exhaust gas specified and an operating status of an engine or the flow Q1 of the gas flowing in the particulate matter catching filter (DPF) 22 of the exhaust line 21, the mass $PM_{enter\ full\ filter}$ (g/h) of the particulate matter flowing into the diesel particulate filter (DPF) 22 is calculated.

The contents of EP1916394A1 are incorporated by reference herein.

SUMMARY OF THE INVENTION

According to an aspect of the present invention, a particulate matter concentration measuring apparatus configured to measure a particulate matter concentration in exhaust gas flowing in an exhaust line of a diesel engine includes an exhaust gas extraction line, a particulate matter detection filter, a heating unit, and a differential pressure detection unit. The exhaust gas extraction line is branched from the exhaust line and has a flow passage cross-sectional area smaller than a flow passage cross-sectional area of the exhaust line. The particulate matter detection filter is provided in the exhaust gas extraction line and configured to catch particulate matter. The heating unit is configured to heat the caught particulate matter. The differential pressure detection unit is configured to detect a differential pressure generated between an inlet and an outlet of the particulate matter detection filter. The heating unit is configured to apply about 50% or more of a calorific value for heating the particulate matter to an area making up about 30% of the particulate matter detection filter on an upstream side of an exhaust gas flow.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
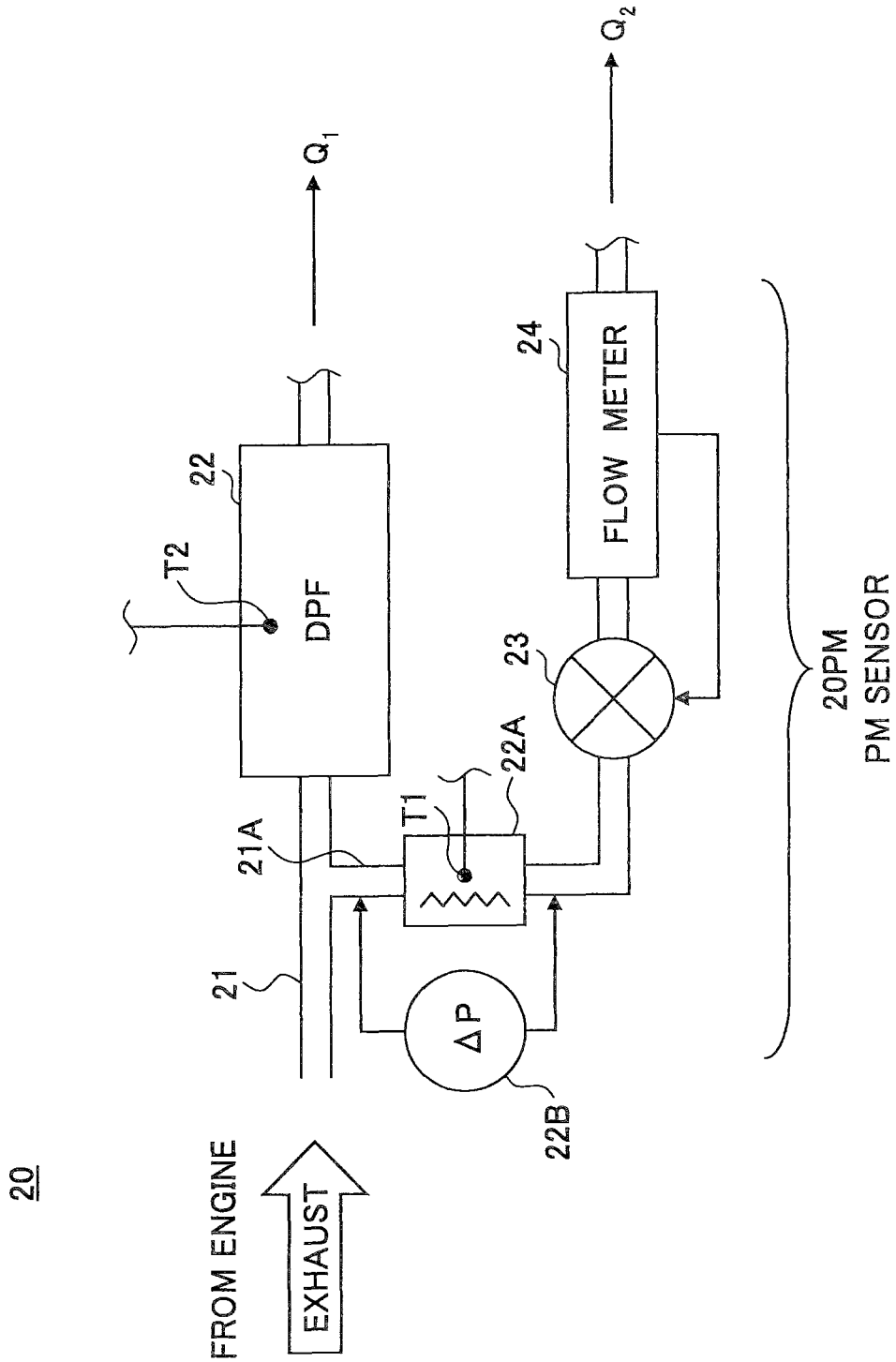
FIG. 1 is a diagram showing the configuration of a conventional exhaust gas purification apparatus.

The embodiments will now be described with reference to the accompanying drawings, wherein like reference numerals designate corresponding or identical elements throughout the various drawings.

(First Embodiment)

Figure 2:
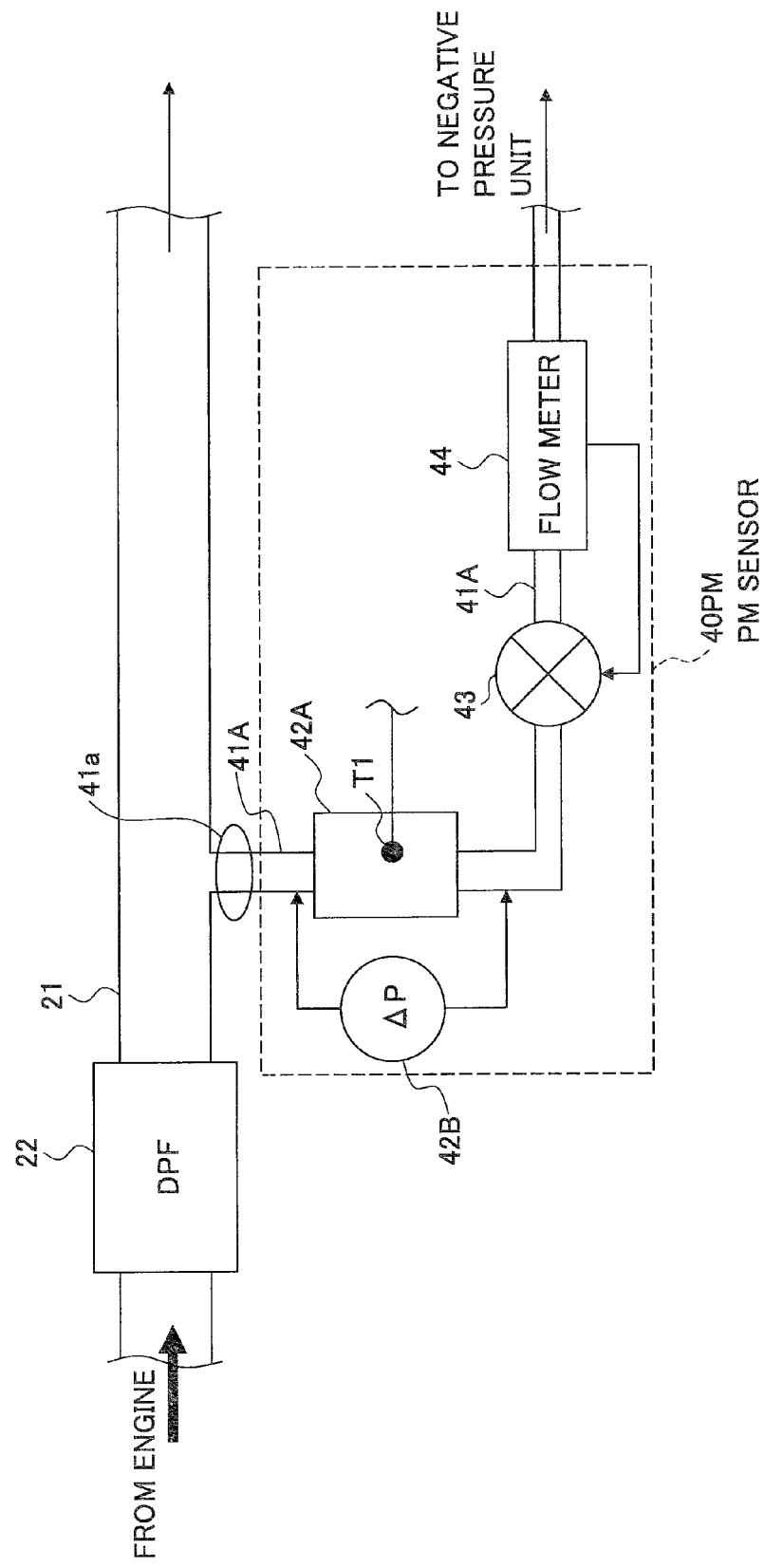
FIG. 2 is a diagram showing the configuration of an exhaust gas purification apparatus using a particulate matter concentration measuring apparatus according to a first embodiment of the present invention.

FIG. 2 shows the configuration of a particulate matter concentration measuring apparatus 40PM (PM sensor) according to a first embodiment of the present invention. Note that components same as those of FIG. 1 are denoted by the same reference numerals and descriptions thereof are omitted. The particulate matter concentration measuring apparatus 40PM of the first embodiment shown in FIG. 2 makes it possible to detect a failure occurring when particulate matter leaks to the downstream side of the particulate matter catching filter (DPF) 22 in the exhaust line 21 at a level more than or equal to a threshold and issue instructions for performing lighting, flashing, etc., of an alarm and a lamp.

Referring to the first embodiment shown in FIG. 2, the exhaust line 21 of a diesel engine, which is provided with the particulate matter catching filter (DPF) 22, is connected to an exhaust gas extraction line 41A having an exhaust gas extraction unit 41a at its one end on the downstream side of the particulate matter catching filter (DPF) 22. The exhaust gas extraction line 41A is connected in series to a particulate matter detection filter 42A of the first embodiment shown in FIG. 3, a flow meter 44 that measures a flow Q2 in the exhaust gas extraction line 41A, and a flow control valve 43. An end part on the downstream side of the exhaust gas extraction line 41A is connected to a unit such as a negative pressure tank and an air intake unit where a pressure is lower than the pressure of the inlet of the particulate matter detection filter 42A, whereby exhaust gas in the exhaust line 21 is suctioned into the particulate matter detection filter 42A. This configuration produces the same effect as when a suction pump is connected to the downstream side of the exhaust gas extraction line 41A, which enables the stable supply of exhaust gas to the particulate matter detection filter 42A.

The particulate matter detection filter 42A is provided with the temperature measuring unit T1 that measures the temperature of the particulate matter detection filter 42A and a differential pressure measuring unit 42B. The differential pressure measuring unit 42B measures the differential pressure $\Delta P$ generated between the front side and the rear side of the particulate matter detection filter 42A. The exhaust gas extraction unit 41a has a flow passage cross-sectional area smaller than that of the exhaust line 21.

Note that as the differential pressure measuring unit 42B, a diaphragm pressure gauge and known pressure meters of a gage type, a bellows type, a thermal type, and the like can be used. As the flow meter 44, known flow meters such as a hotwire flow meter and a venturi meter can be used.

Figure 3:
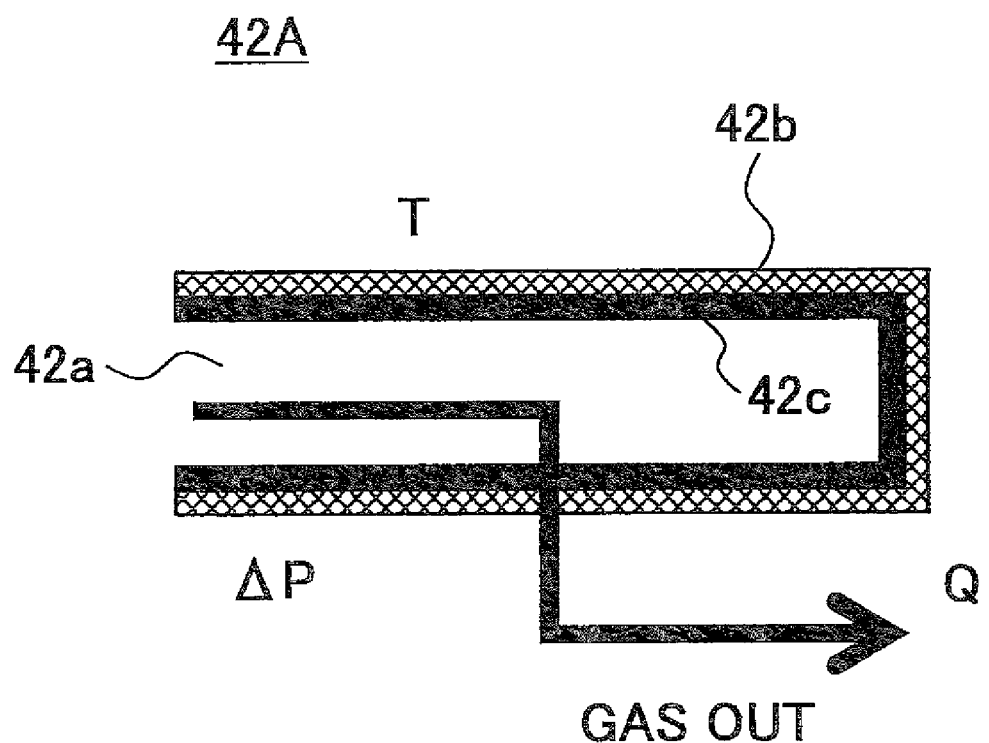
FIG. 3 is a diagram for explaining the function of a particulate matter detection filter in the particulate matter concentration measuring apparatus according to the first embodiment of the present invention.
Figure 12:
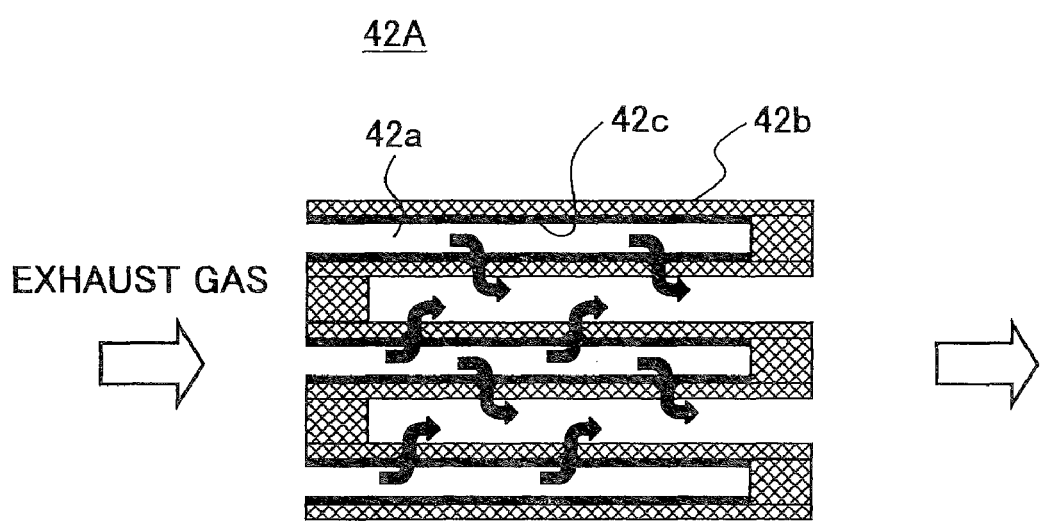
FIG. 12 is a diagram showing the configuration of the particulate matter detection filter according to the modified example according to the first embodiment of the present invention.

FIG. 3 shows an example of the particulate matter detection filter 42A according to the first embodiment of the present invention. In the example shown in FIG. 3, the particulate matter detection filter 42A has only a single cell 42b. However, as shown in the first embodiment in FIG. 12, the particulate matter detection filter 42A may have the plural cells 42b.

Referring to the first embodiment of the present invention shown in FIG. 3, the particulate matter detection filter 42A includes one or more gas passages 42a, which have a volume of about 5% or less, e.g., about 0.05 through about 5% of the total volume of an exhaust gas passage in the particulate matter catching filter (DPF) 22, have a volume of about 65 ml or less, e.g., about 0.05 through about 65 ml, or have a filtration area of about 0.1 through about 1000 cm$^2$ (preferably a filtration area of about 1 through about 10 cm$^2$), such that their cross sectional areas are formed in, e.g., rectangles and either ends of the gas passages 42a are closed (rear side is closed in the case of one cell).

Referring to the first embodiment of the present invention shown in FIG. 3, the cell 42b made of porous ceramics has the gas passage 42a with its one end opened and the other end closed. The exhaust gas introduced in the gas passage 42a passes through a cell wall made of porous ceramics and moves to an adjacent gas passage. At that time, particulate matter is caught at the inner wall surface of the cell 42b, which in turn forms a particulate matter layer 42c on the inner wall surface.

Figure 4:
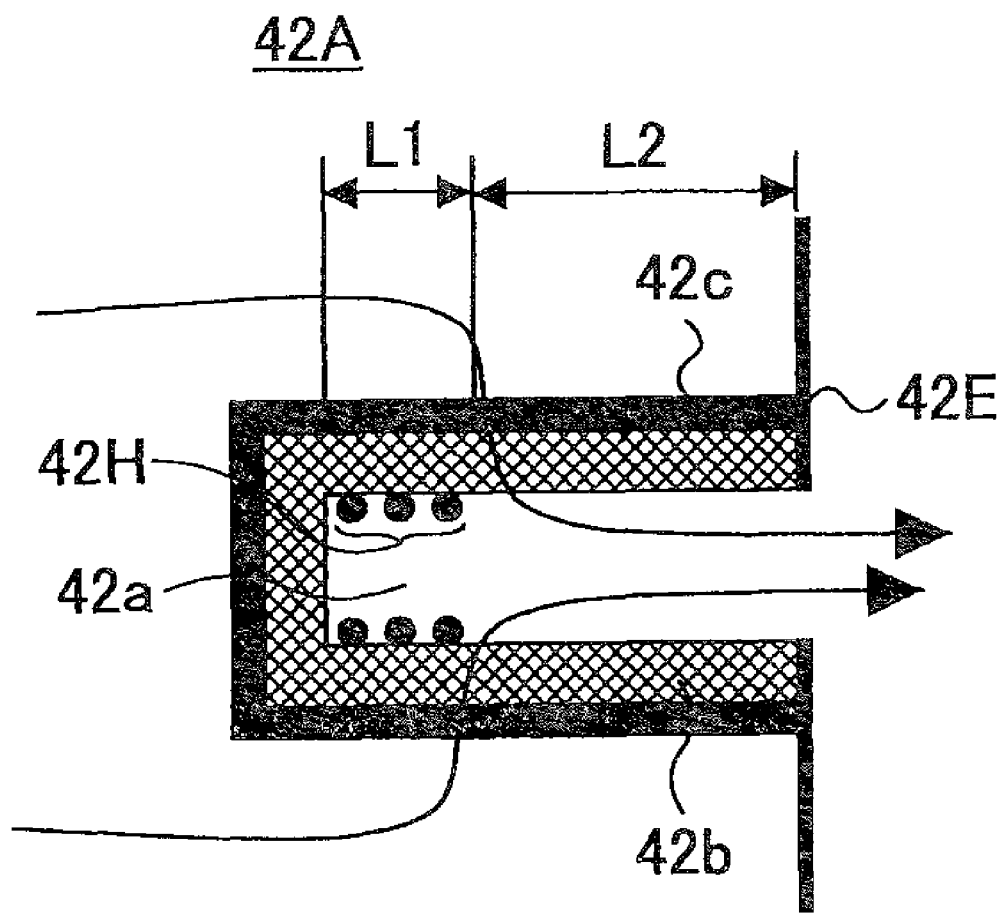
FIG. 4 is a diagram showing a modified example of the particulate matter detection filter in the particulate matter concentration measuring apparatus according to the first embodiment of the present invention.

FIG. 4 shows a modified example of the cell 42b according to the first embodiment of the present invention shown in FIG. 3. In the cell shown in FIG. 4, exhaust gas passes through a cell wall from the outside of the cell and flows into the gas passage 42a. At that time, the particulate matter layer 42c is accumulated on the outer surface of the cell 42b. In the filter according to the first embodiment of the present invention shown in FIG. 12, the cells shown in FIG. 3 and those shown in FIG. 4 are alternately arranged so as to be adjacent to each other.

Note that similar cells are also formed in the conventional particulate matter catching filter (DPF) 22 described in FIG. 1. The gas passage 42a and the cell 42b are not necessarily approximately the same in size and in cross-sectional shape as the gas passage in the particulate matter catching filter (DPF) 22, but may be in any cross-sectional shape such as approximately circle, approximately square, approximately octagon, and approximately ellipse. Furthermore, the material of the porous ceramics constituting the particulate matter detection filter 42A (cell 42b) is not necessarily approximately the same as that of the porous ceramics constituting the particulate matter catching filter (DPF) 22, and may not be made of ceramics. If the total volume of the gas passage 42a is set to approximately 5% or less of the total volume of the exhaust gas passage in the particulate matter catching filter (DPF) 22, have a volume of about 65 ml or less, or have a filtration area of about 0.1 through about 1000 cm$^2$ (preferably a filtration area of about 1 through about 10 cm$^2$), a uniform soot layer is accumulated on the cell 42b. Accordingly, as described below, the accumulated amount of the particulate matter in the particulate matter catching filter (DPF) 22 can be easily and correctly measured.

The particulate matter concentration measuring apparatus 40PM according to the first embodiment of the present invention shown in FIG. 2 calculates the accumulated amount of the particulate matter caught by the particulate matter detection filter 42A based on the following formula 1.

$$\Delta P = \frac{\mu Q}{2 V trap}(\alpha + Ws)^2 \left[ \frac{Ws}{Kw\alpha} + \frac{1}{2Ksoot}\ln\left(\frac{\alpha}{\alpha - 2W}\right) + \frac{4FL^2}{3}\left(\frac{1}{(\alpha - 2W)^4} + \frac{1}{\alpha^4}\right) \right] + \frac{\rho Q^2(\alpha + Ws)^4}{V trap^2}\left[ \frac{\beta Ws}{4} + 2\zeta\left[\frac{L}{\alpha}\right]^2 \right]$$

(Formula 1)

where "ΔP" is a differential pressure expressed in units of (Pa), "μ" is a kinematic viscosity coefficient expressed in units of (Pa·s), "Q" is an exhaust gas flow expressed in units of (m³/s), "α" is the length of a side of a cell expressed in units of (m), "ρ" is an exhaust gas density expressed in units of (g/m³), "$V_{trap}$" is a filter volume expressed in units of (m³), "$W_s$" is a wall thickness expressed in units of (m), "$K_w$" is the gas permeability of a wall expressed in units of (m⁻¹), "$K_{soot}$" is the gas permeability of a caught particulate-matter-layer expressed in units of (m), "W" is the thickness of a caught particulate-matter-layer expressed in units of (m⁻¹), "F" is a coefficient (=28.454), "L" is an effective filter length expressed in units of (m), "β" is a Forchheimer coefficient of a porous wall expressed in units of (m⁻¹), and "ξ" is a differential pressure due to passing through of gas in units of (Pa).

Next, the mass "$m_{soot}$" of the particulate matter caught by the particulate matter detection filter 42A (cell 42b) is found based on the following formula 2.

$$W = \frac{\alpha - \sqrt{\alpha^2 - \frac{msoot}{Ncells \times L \times \rho soot}}}{2} \quad \text{(Formula 2)}$$

where "$m_{soot}$" is the mass (g) of the caught particulate matter, "$N_{cells}$" is the opening number of a cell on the side of the inlet, and "$\rho_{soot}$" is the density of the caught particulate matter.

The caught amount "PM" (g/s) of the particulate matter per unit time can be found by dividing "$m_{soot}$" by an elapsed time (s) since the previous regeneration of the particulate matter detection filter 42A.

When the mass "PM" (g/s) of the particulate matter accumulated per unit time is found, a particulate matter concentration "$PM_{conc}$" (g/m³) in exhaust gas is found based on the following formula 3 using a flow "Q2" (m³/s) of the exhaust gas passing through the particulate matter detection filter 22A.

(Formula 3)

$$PM[g/s]=Mconc[g/m^3] \times Q2[m^3/s] \quad \text{formula (3)}$$

As shown in the first embodiment of the present invention in FIG. 2, according to the embodiment of the present invention, the particulate matter concentration measuring apparatus 40PM arranged on the downstream side of the particulate matter catching filter (DPF) 22 makes it possible to immediately detect a failure occurring when the particulate matter leaks to the downstream side of the particulate matter catching filter (DPF) 22 in the exhaust line 21 at a level more than or equal to a threshold and issue instructions for performing lighting, flashing, etc., of an alarm and a lamp.

Meanwhile, in the particulate matter concentration measuring apparatus 40PM in the configuration according to the first embodiment of the present invention shown in FIG. 2, the particulate matter is accumulated on the particulate matter detection filter 42A with time. Therefore, as shown in the first embodiment of the present invention in FIG. 5, a heater 42h is provided on the particulate matter detection filter 42A (cell 42b) according to the embodiment of the present invention. The particulate matter mainly containing C (carbon) and caught by the cell 42b is burned when the heater 42h is driven as occasion demands. Thus, the particulate matter detection filter 42A is regenerated.

Figure 5:
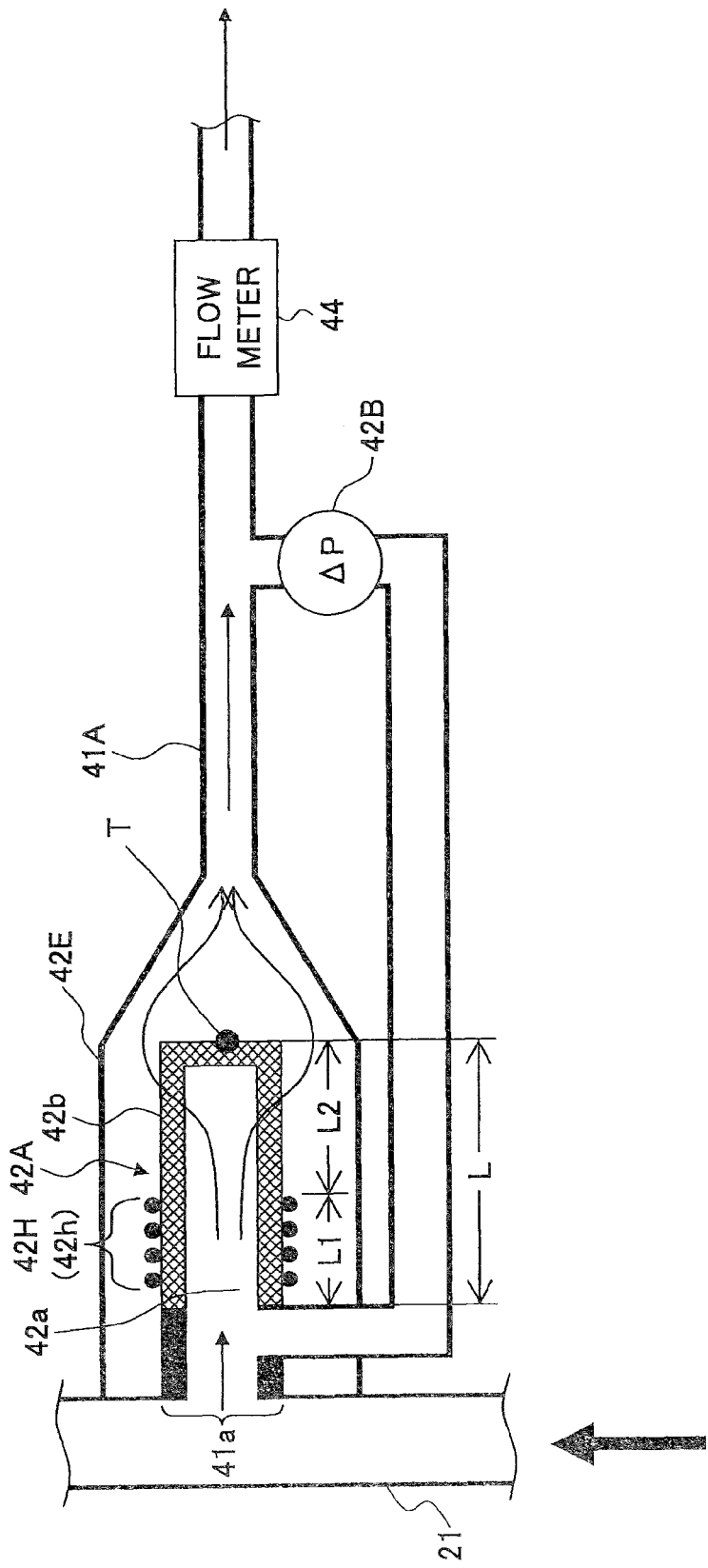
FIG. 5 is a diagram specifically showing the configuration of the particulate matter concentration measuring apparatus according to the first embodiment of the present invention.

FIG. 5 is a diagram specifically showing the configuration of the particulate matter concentration measuring apparatus 40PM according to the first embodiment of the present invention shown in FIG. 2.

Referring to the first embodiment of the present invention shown in FIG. 5, the particulate matter detection filter 42A has one end constituting the exhaust gas extraction unit 41a and is stored in a housing connected to the exhaust gas extraction line 41A. Furthermore, a diaphragm pressure meter constituting the differential pressure measuring unit 42B is provided on the downstream side of the particulate matter detection filter 42A. The differential pressure measuring unit 42B has one end connected to the upstream side of the particulate matter detection filter 42A and the other end connected to the exhaust line extraction line 41A on the downstream side of the particulate matter detection filter 42A. With this configuration, the differential pressure measuring unit 42B can measure a differential pressure generated between the front side and the rear side of the cell 42b constituting the particulate matter detection filter 42A.

The cell 42b has a length L from an end on the upstream side to an end on the downstream side in the flow direction of the exhaust gas passing through the cell 42b. In the particulate matter concentration measuring apparatus 40PM according to the first embodiment of the present invention shown in FIG. 5, a heating unit 42H composed of the heater 42h, which burns the particulate matter accumulated in the cell 42b to regenerate the particulate matter detection filter 42A, is densely arranged in an upstream-side region L1 making up, e.g., about 30% of the cell constituting the particulate matter detection filter 42A on the upstream side. In this configuration, the heating unit 42H is not provided in a downstream-side region L2 on the downstream side of the upstream-side region L1. Alternatively, the heating unit 42H is provided so as to generate heat lower than that generated in the upstream-side region L1.

Figure 6:
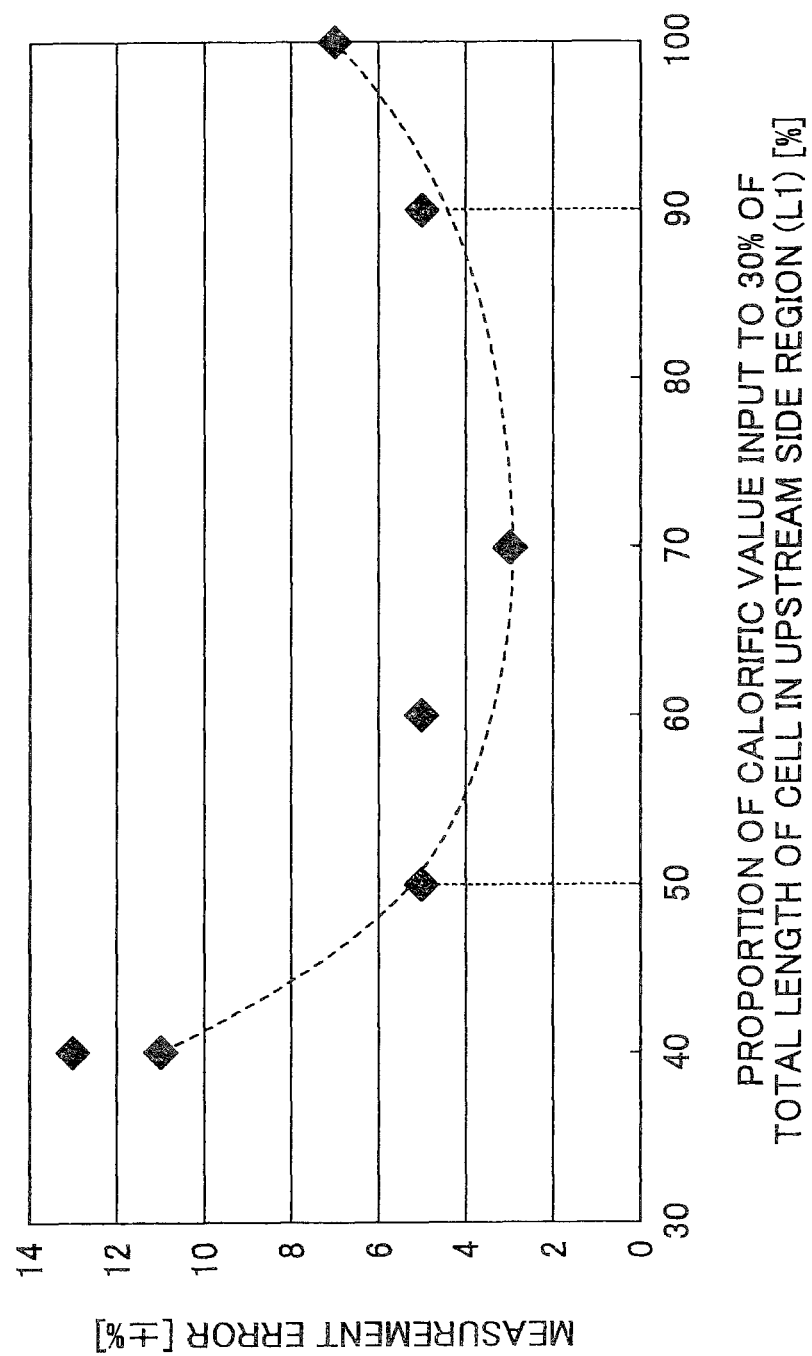
FIG. 6 is a graph showing a relationship between the proportion of a calorific value input to an upstream-side region of a cell and a measurement error in the particulate matter concentration measuring apparatus according to the first embodiment of the present invention.

FIG. 6 is a graph showing cases in which the proportion (%) of calorific value (electric power) input to the upstream-side region L1 of the cell 42b to that input to the entire cell is changed in various ways using the cells according to the first embodiment of the present invention schematically shown in FIGS. 7A through 7D as the cell 42b. That is, FIG. 6 is a graph showing measurement errors between a particulate matter concentration in exhaust gas found according to the above formulae 1 through 3 and a particulate matter concentration (actual value) found by measuring particulate matter actually contained in exhaust gas. Note that in an experimental example shown in FIG. 6, the upstream-side region L1 is set to make up 30% of the entire length L.

Figure 7A:
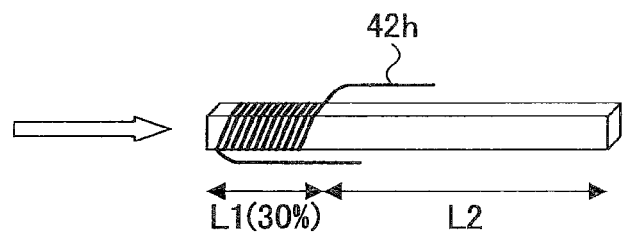
FIG. 7A is a diagram showing an example of a heating unit according to the first embodiment of the present invention.
Figure 7B:
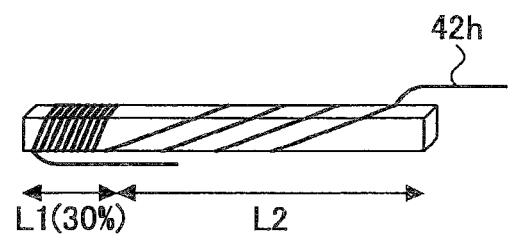
FIG. 7B is a diagram showing other example of the heating unit according to the first embodiment of the present invention.

Referring to samples shown in FIGS. 7A and 7B, the cell 42b has an entire length L of 15 mm and a square cross section, a side of which is 4.0 mm. In the cell 42b, a gas passage having a square cross section, a side of which is 3.2 mm, is provided as the gas passage 42a. The cell 42b has a wall thickness of 0.4 mm. In the example of the cell shown in FIG. 7A, the wire heater (kanthal wire heater) 42h is wound around only the upstream-side region L1 eight times as the heating unit 42H. On the other hand, in the cell shown in FIG. 7B, the wire heater (kanthal wire heater) 42h is wound around the upstream-side region L1 twelve times and wound around the downstream-side region L2 six times.

Figure 7C:
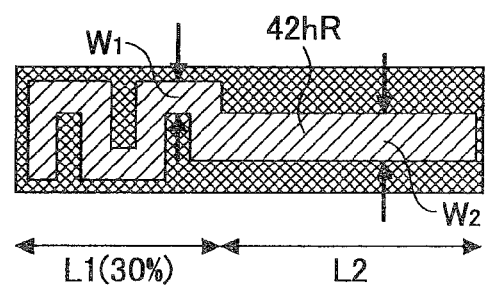
FIG. 7C is a diagram showing still other example of the heating unit according to the first embodiment of the present invention.

In the samples shown in FIGS. 7C and 7D, a resistance heater pattern 42hR is provided on the same cell 42b as those shown in FIGS. 7A and 7B by thermal-spraying or printing a Cr film or by sputtering a Pt film (see table 1 below). In the example of the sample shown in FIG. 7C, the resistance heater pattern 42hR is formed such that its width is shaped like a zigzag pattern having a width of 0.8 mm in the region L1 and shaped like a linear pattern having a width of 1.2 mm in the region L2. The same heater pattern 42hR is also provided at the opposing surface of the cell 42b. In the sample shown in FIG. 7C, the proportion (%) of a calorific value input to the region L1 is varied by changing the width W1 in the region L1 and the width W2 in the region L2 of the resistance heater pattern 42hR to, e.g., 0.8 mm and 1.2 mm, or by changing the number of folding times of the zigzag pattern of the resistance heater pattern 42hR, the pitch of the zigzag pattern, or the thickness of heater patterning.

Figure 7D:
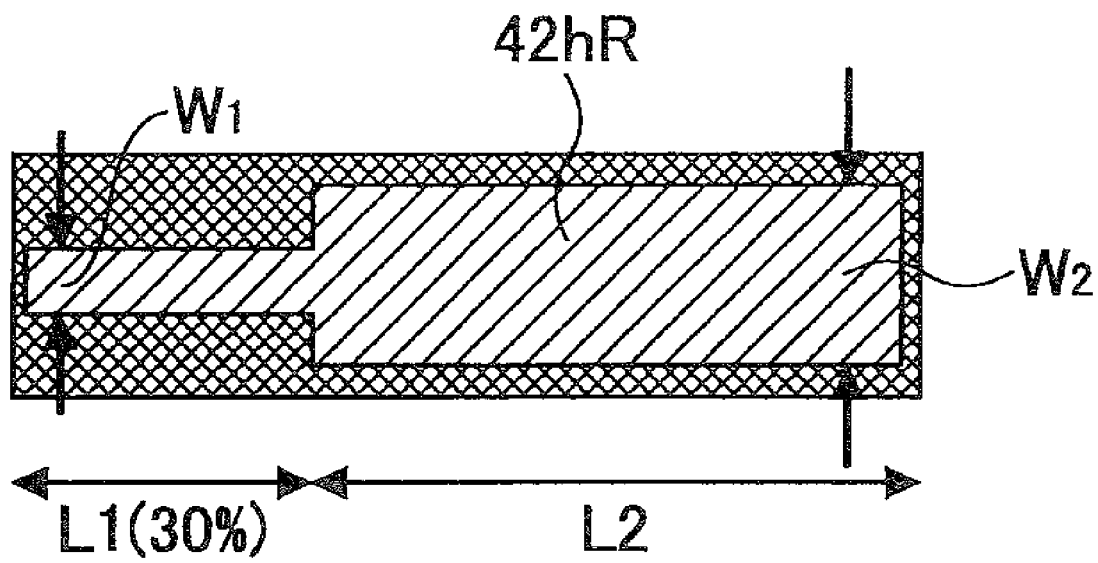
FIG. 7D is a diagram showing yet other example of the heating unit according to the first embodiment of the present invention.

In the sample shown in FIG. 7D, the resistance heater pattern 42hR is formed in a linear shape in the regions L1 and L2 such that the widths W1 and W2 are different in the regions L1 and L2, respectively. In an example, the widths W1 and W2 are set to 0.93 mm and 3.7 mm, respectively.

In the experimental example shown in FIG. 6 described below, the number of winding times of the wire heater (kanthal wire heater) 42h is changed in the upstream-side region L1 and the downstream-side region L2 to vary the proportion (%) of the calorific value input to the upstream-side region L1 at the regeneration of the particulate matter detection filter 42A in various ways. Furthermore, exhaust gas is introduced in the cell 42b at a ratio (%) of 0.141 l per minute.

Figure 8:
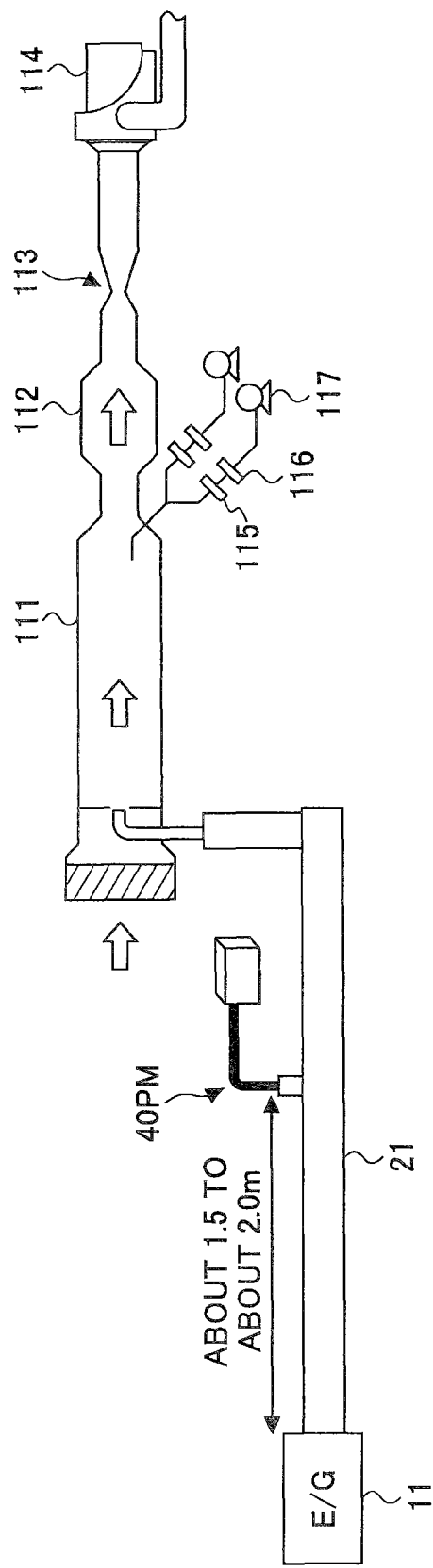
FIG. 8 is a diagram for explaining an experimental example by which the actual value of a particulate matter concentration in the graph of FIG. 6 is found.

As shown in FIG. 8, exhaust gas from a diesel engine 11 to the exhaust line 21 is guided to a dilution tunnel 111 in which clean air is introduced, then diluted and cooled up to temperature below 52° C., and collected on a primary collecting filter 115 and a secondary collecting filter 116. The mass of the collected exhaust gas is measured by a microbalance to actually measure particulate matter contained in the exhaust gas. The measured particulate matter is converted into the concentration of the exhaust line 21 and recognized as an actual value. A calculated value ($PM_{conc}$) by the particulate matter concentration measuring apparatus 40PM (distance from diesel engine (E/G) is 1.5 through 2.0) provided in the exhaust line 21 is compared with the actual value to find a measurement error. Note that according to configuration shown in FIG. 8, the exhaust gas is suctioned by a blower 114 via a heat exchanger 112 and a critical flow venturi tube 113 after passing through the dilution tunnel 111. Furthermore, a blower 117 is also provided on the downstream side of the primary collecting filter 115 and the secondary collecting filter 116 to suction the exhaust gas.

Referring back to the graph shown in FIG. 6, if the calorific value is intensively input to the downstream-side region L2, i.e., if the proportion (%) of the calorific value input to the upstream-side region L1 making up 30% of the cell 42b on the upstream side is set to 40% of the calorific value input to the entire cell, it is found that the measurement error of the particulate matter concentration by the particulate matter concentration measuring apparatus 40PM approximates a great measurement error of ±11% or ±13% beyond ±10%.

Conversely, if the proportion (%) of the calorific value input to the upstream-side region L1 making up 30% of the cell 42b on the upstream side is set to 50% through 70% of the calorific value input to the entire cell, it is found that the measurement error reduces to less than ±6% as shown in FIG. 6.

On the other hand, if the calorific value input to the upstream-side region L1 making up 30% of the cell 42b on the upstream side is set to 100% of the calorific value input to the entire cell, it is found that the measurement error increases again, exceeding ±6%.

Table 1 shows regeneration rates and measurement errors when various materials are used to form the wire heater (kanthal wire heater) 42h or the resistance heater pattern 42hR in the cell 42b and the ratio of the calorific value input to the upstream-side region L1 and the downstream-side region L2 is changed in many ways.

TABLE 1

MEASURED AFTER REGENERATION

| | PROPORTION (%) OF THE CALORIFIC VALUE INPUT TO FRONT 30% OF TOTAL LENGTH OF CELL (L1) | PROPORTION (%) OF THE CALORIFIC VALUE INPUT TO FRONT 30% OF TOTAL LENGTH OF CELL (L2) | FORMING METHOD | MATERIAL | REGENERATION RATE [%] | MEASUREMENT ERROR [±%] |
|---|---|---|---|---|---|---|
| EXAMPLE 1 | 70 | 30 | THERMAL SPRAYING | Cr | 96 | 3 |
| EXAMPLE 2 | 50 | 50 | THERMAL SPRAYING | Cr | 87 | 5 |
| EXAMPLE 3 | 60 | 40 | THERMAL SPRAYING | Cr | 93 | 5 |
| EXAMPLE 4 | 100 | 0 | THERMAL SPRAYING | Cr | 85 | 7 |
| EXAMPLE 5 | 60 | 40 | WINDING | KANTHAL WIRE | 90 | 5 |
| EXAMPLE 6 | 60 | 40 | SPUTTERING | Pt | 92 | 5 |
| EXAMPLE 7 | 60 | 40 | PRINTING | Cr | 93 | 5 |
| EXAMPLE 8 | 90 | 10 | THERMAL SPRAYING | Cr | 90 | 5 |
| COMPARATIVE EXAMPLE 1 | 40 | 60 | THERMAL SPRAYING | Cr | 78 | 11 |
| COMPARATIVE EXAMPLE 2 | 40 | 60 | WINDING | KANTHAL WIRE | 75 | 13 |

Referring to table 1, the "regeneration rate" refers to the amount of particulate matter remaining after the wire heater (kanthal wire heater) 42h or the resistance heater pattern 42hR is driven to burn the particulate matter accumulated in the cell 42b to regenerate the particulate matter detection filter 42A. The regeneration rate is found by comparing the initial weight of the cell 42b with the weight of the cell 42b after the regeneration of the particulate matter detection filter 42A. The measurement error is found as in the case shown in FIG. 6.

As shown in table 1, the measurement error increases as the regeneration rate reduces. This would lead to the fact that a reason for the measurement error in the graph shown in FIG. 6 is caused by the remaining of unburned particulate matter in the cell 42b even after the regeneration of the particulate matter detection filter 42A.

Particularly, in the experimental example in the graph shown in FIG. 6 in which the calorific value input to the upstream-side region L1 of the cell is 40% of the calorific value input to the entire cell, 60% of the calorific value input to the entire cell is input to the downstream-side region L2. As a result, the particulate matter in the upstream-side region L1 is not sufficiently burned, and the unburned particulate matter remains even in the downstream-side region L2. For this reason, the large measurement error occurs in the measurement of the particulate matter concentration in the experimental example.

Conversely, if the calorific value input is properly distributed to the upstream-side region L1 and the downstream-side region L2, i.e., if the proportion (%) of the calorific value input to the upstream-side region L1 to that input to the entire cell is 50% or more to 90% or less, the measurement error in the particulate matter concentration can be reduced to ±6% or less.

Furthermore, if 100% of the calorific value is input to only the upstream-side region L1 in the graph shown in FIG. 6, the value of the measurement error increases again. This is because if no calorific value is input to the downstream-side region L2, burning of the particulate matter is relied only on the heat transmitted into the particulate matter collecting filter. Therefore, the heat applied to the downstream side L2 becomes reduced, which causes the insufficient burning of the particulate matter in the downstream side region L2 at the regeneration of the particulate matter detection filter 42A. As a result, the measurement error increases.

According to the embodiment of the present invention, the heating unit 42H is densely arranged in a part of the particulate matter detection filter 42A as shown in the first embodiment of the present invention in FIG. 5 or FIGS. 7A through 7D. This arrangement makes it possible to satisfactorily regenerate the particulate matter detection filter 42A and reduce the measurement error in the particulate matter concentration detection apparatus 40PM.

Furthermore, as shown in table 1, the heating unit 42H can be (a resistance pattern) made of a wire heater (kanthal wire), a Cr film, or a Pt film, but the material of the heating unit 42H is not limited to them. Moreover, as shown in table 1, the resistance heater pattern 42hR can be formed by the use of various methods such as thermal spraying, sputtering, printing, and particularly screen printing.

Examples of the wire heater include a kanthal wire, but other wire heaters may be used. Furthermore, the wire heater and the resistance pattern are also called resistance heaters. The resistance heaters are not limited to the wire heater and the resistance pattern.

Figure 9:
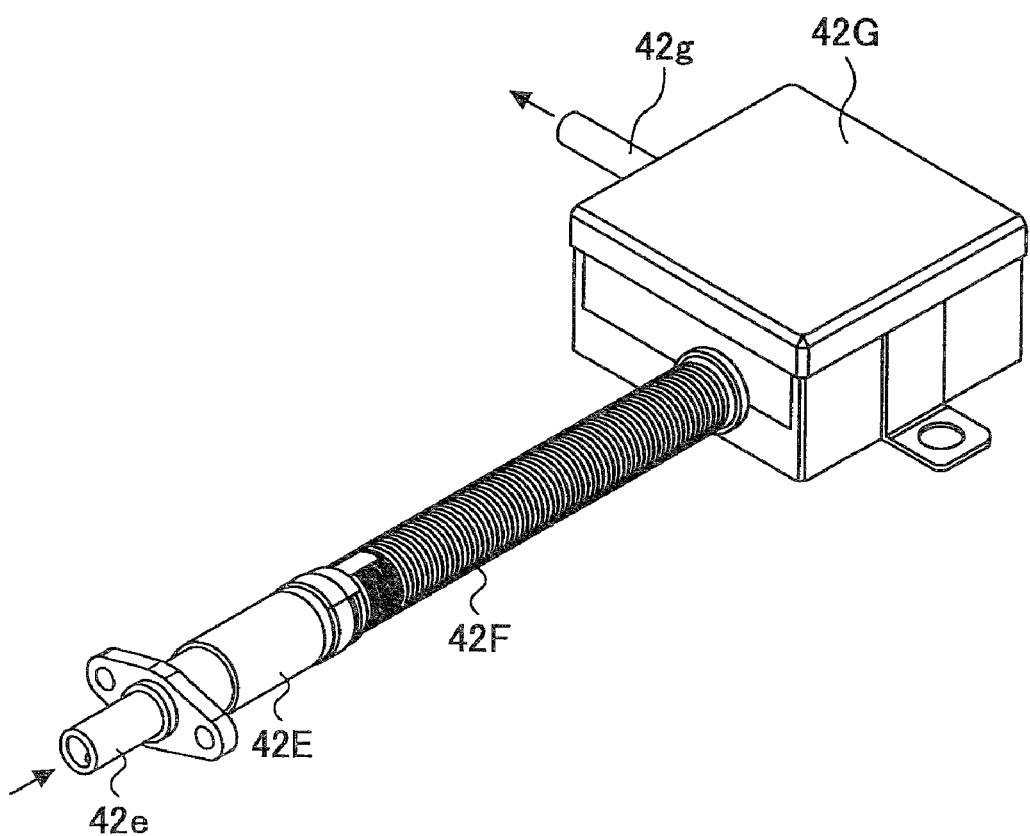
FIG. 9 is a diagram showing the whole of a particulate matter concentration measuring apparatus according to a second embodiment of the present invention.

Note that a particulate matter concentration measuring apparatus 40PM according to the embodiment shown in FIG. 9 is inserted into the exhaust line 21 shown in FIG. 2 on the downstream side of the particulate matter catching filter (DPF) 22. The particulate matter concentration measuring apparatus 40PM has a pipe-shaped housing 42E that is provided with a fixed head unit 42e and made of heat-resistant metal such as stainless steel. The housing 42E includes the particulate matter detection filter 42A preferably made of porous ceramics such SiC (silicon carbide). Here, the head unit 42e constitutes a part of the exhaust gas extraction line 41A inserted into the exhaust line 21.

As shown in this embodiment in FIG. 9, a flexible hose 42F through which exhaust gas passes is extended from the housing 42E. At an end on the downstream side of the flexible hose 42F, a control unit 42G storing the differential pressure measuring unit 42B and the flow measuring unit 44 is provided. The exhaust gas having passed through the control unit 42G is exhausted to an exhaust pipe 42g.

This configuration enables a desired particulate matter concentration measuring apparatus to be downsized. As a result, the particulate matter concentration measuring apparatus can be installed in any position of a vehicle as occasion demands.

Figure 10:
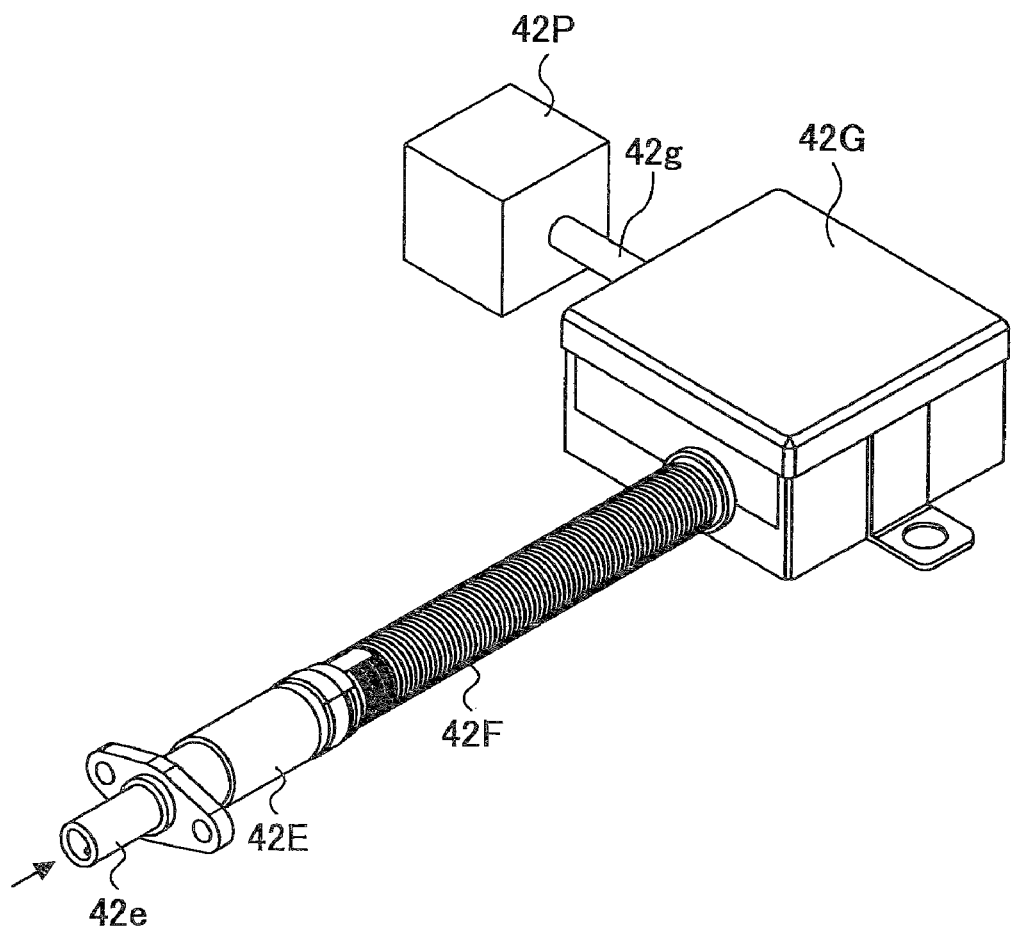
FIG. 10 is a diagram showing a modified example of the particulate matter concentration measuring apparatus according to the first embodiment of the present invention.

As shown in the first embodiment of the present invention in FIG. 10, according to the embodiment, a pump 42P may be connected to the exhaust pipe 42g according to the first embodiment of the present invention shown in FIG. 9 that exhausts the exhaust gas from the control unit 42G so as to forcibly exhaust the exhaust gas. With this configuration, even if the head unit 42e is provided in an atmosphere in which the exhaust gas does not flow, the exhaust gas is suctioned by a negative pressure generated by the pump 42P, whereby the particulate matter concentration can be desirably measured.

(Second Embodiment)

Figure 11:
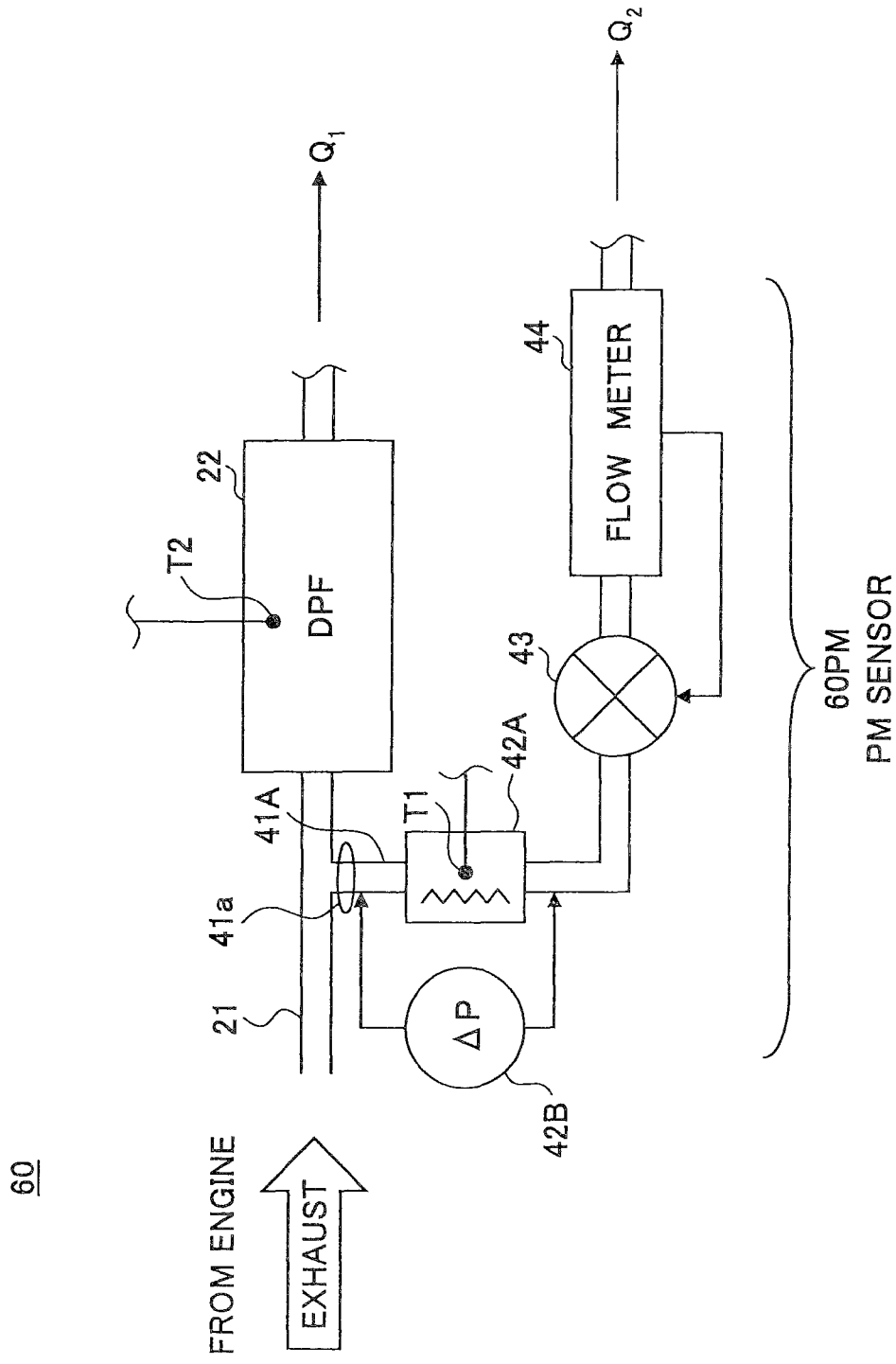
FIG. 11 is a diagram showing the configuration of an exhaust gas purification apparatus using the particulate matter measuring apparatus according to the second embodiment of the present invention.

FIG. 11 shows the configuration of an exhaust gas purification apparatus 60 of a diesel engine having a particulate matter detection apparatus 60PM (PM sensor) according to a second embodiment of the present invention.

Referring to the second embodiment of the present invention shown in FIG. 11, the exhaust gas purification apparatus 60 has a configuration similar to the configuration of the conventional exhaust gas purification apparatus 20 shown in FIG. 1. That is, the exhaust gas purification apparatus 60 has an exhaust gas extraction line 41A branched from the exhaust line 21 on the upstream side of the particulate matter catching filter (DPF) 22.

In the configuration of the second embodiment of the present invention shown in FIG. 11, exhaust gas that does not pass through the particulate matter catching filter (DPF) 22 is caught by a particulate matter detection filter 42A, and the following processing is performed in addition to the processing according to the above formulae 1 through 3 based on the amount of the particulate matter caught by the particulate matter detection filter 42A.

The particulate matter concentration "$PM_{conc}$" in the exhaust gas is the same both in the exhaust gas extraction line 41A and the exhaust line 21. Therefore, the amount ($PM_{enter\ full\ filter}$ (g/h)) of the particulate matter that passes through the exhaust line 21 is found according to the following formula 4.

$$PM_{enter\ full\ filter}\ (g/h) = PM_{conc}\ (g/m^3) \times Q1\ (m^3/h) \quad \text{(Formula 4)}$$

where Q1 is an exhaust gas flow in the exhaust line 21.

According to this formula, the amount of the particulate matter accumulated in the particulate matter catching filter (DPF) 22 can be estimated. Note, however, that Q1 is the flow of the exhaust gas that passes through the particulate matter catching filter (DPF) 22. Q1 may be found by actually measuring the flow of the exhaust gas or may be found by estimating the operating condition of an engine.

In the configuration of the second embodiment of the present invention shown in FIG. 11, a valve 43 is further provided in the exhaust gas extraction line 41A. The valve 43 is controlled by a flow meter 44 as in the case of the exhaust gas purification apparatus 20 shown in FIG. 1, whereby the flow of the exhaust gas in the exhaust gas extraction line 41A is controlled to a predetermined value Q2.

In this configuration, however, the particulate matter is accumulated on the particulate matter detection filter 42A with time. Therefore, the particulate matter detection filter 42A is regenerated.

According to this embodiment, the heater 42h is provided on the particulate matter detection filter 42A (cell 42b) as described above. The heater 42h is driven by power from a driving line as occasion demands. Thus, the particulate matter mainly containing C (carbon) caught by the cell 42b is burned to regenerate the particulate matter detection filter 42A.

This embodiment can also provide the same effects as those provided by the first embodiment.

The present invention is not limited to the specifically disclosed embodiment, but variations and modifications may be made without departing from the scope of the present invention. For example, the flow measuring unit according to the embodiment can be eliminated if the flow of exhaust gas in the exhaust gas extraction line is known in advance. Furthermore, the temperature measuring unit may be eliminated provided that the characteristics of exhaust gas are constant. Moreover, the valve can be eliminated if the flow of exhaust gas is correctly measured.

Furthermore, as shown in the first embodiment of the present invention in FIG. 4, a heating unit (heater) may be arranged inside the cell (on an inner periphery) or a heating unit (heater) may be arranged outside the cell (on an outer periphery).

According to the embodiments of the present invention, the uniform and effective regeneration of a particulate matter detection filter is ensured, which results in an improvement in the measurement accuracy of a particulate matter concentration.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A particulate matter concentration measuring apparatus configured to measure a particulate matter concentration in exhaust gas flowing in an exhaust line of a diesel engine, the apparatus comprising:
   an exhaust gas extraction line that is branched from the exhaust line and has a flow passage cross-sectional area smaller than a flow passage cross-sectional area of the exhaust line;
   a particulate matter detection filter that is provided in the exhaust gas extraction line and configured to catch particulate matter;
   a heating unit configured to heat the caught particulate matter; and
   a differential pressure detection unit configured to detect a differential pressure generated between an inlet and an outlet of the particulate matter detection filter, wherein the heating unit is configured to apply 50% or more of a calorific value for heating the particulate matter to an area making up 30% of the particulate matter detection filter on an upstream side of an exhaust gas flow.

2. The particulate matter concentration measuring apparatus according to claim 1, wherein
   the heating unit is configured to apply 50% or more to 90% or less of the calorific value for heating the particulate matter to the area making up 30% of the particulate matter detection filter on the upstream side of the exhaust gas flow.

3. The particulate matter concentration measuring apparatus according to claim 1, wherein
   the particulate matter detection filter has at least a cylindrical part extending in an axial direction toward a downstream side of the exhaust gas flow and a bottom part arranged on the downstream side of the exhaust gas flow in the cylindrical part, and the heating unit is provided on an outer periphery of the cylindrical part.

4. The particulate matter concentration measuring apparatus according to claim 1, wherein
   the particulate matter detection filter has at least a cylindrical part extending in an axial direction toward a downstream side of the exhaust gas flow and a bottom part arranged on the upstream side of the exhaust gas flow in the cylindrical part, and the heating unit is provided on an inner periphery of the cylindrical part.

5. The particulate matter concentration measuring apparatus according to claim 1, wherein
   the heating unit comprises a resistance heater wound around the particulate matter detection filter.

6. The particulate matter concentration measuring apparatus according to claim 1, wherein
   the heating unit comprises a resistance heater printed on the particulate matter detection filter.

7. The particulate matter concentration measuring apparatus according to claim 1, wherein
   the heating unit comprises a resistance heater thermally sprayed on the particulate matter detection filter.

8. The particulate matter concentration measuring apparatus according to claim 1, wherein
   the heating unit comprises a resistance heater sputtered on the particulate matter detection filter.

9. The particulate matter concentration measuring apparatus according to claim 1, further comprising
   a flow measuring unit that is inserted in the exhaust gas extraction line and configured to measure the exhaust gas flow in the exhaust gas extraction line.

10. The particulate matter concentration measuring apparatus according to claim 9, further comprising:
    a flow control valve that is inserted in the exhaust gas extraction line and configured to control the exhaust gas flow in the exhaust gas extraction line; and
    a control unit configured to control the flow control valve based on the exhaust gas flow measured by the flow measuring unit and control the exhaust gas flow in the exhaust gas extraction line to a predetermined value.

11. The particulate matter concentration measuring apparatus according to claim 1, further comprising
    a pump arranged on a downstream side of the exhaust gas flow in the particulate matter detection filter.

12. The particulate matter concentration measuring apparatus according to claim 1, further comprising
    a particulate matter catching filter having a capacity greater than a capacity of the particulate matter detection filter and arranged in the exhaust line.

13. The particulate matter concentration measuring apparatus according to claim 12, wherein the exhaust gas extraction line is connected to a downstream side of the particulate matter catching filter in the exhaust line.

14. The particulate matter concentration measuring apparatus according to claim 12, wherein the exhaust gas extraction line is connected to the upstream side of the particulate matter catching filter in the exhaust line.

* * * * *